(12) United States Patent
Deac

(10) Patent No.: US 10,953,198 B2
(45) Date of Patent: Mar. 23, 2021

(54) CENTERING COILED GUIDE

(71) Applicant: Medtronic CryoCath LP, Toronto (CA)

(72) Inventor: Ioana Deac, Vaudreuil-Dorion (CA)

(73) Assignee: Medtronic CryoCath LP, Toronto (CA)

( * ) Notice: Subject to any disclaimer, the term of this patent is extended or adjusted under 35 U.S.C. 154(b) by 592 days.

(21) Appl. No.: 15/816,412

(22) Filed: Nov. 17, 2017

(65) Prior Publication Data

US 2018/0071491 A1 Mar. 15, 2018

Related U.S. Application Data

(63) Continuation of application No. 14/518,545, filed on Oct. 20, 2014, now Pat. No. 9,839,766.

(51) Int. Cl.
| | | |
|---|---|---|
| *A61M 25/01* | (2006.01) | |
| *A61M 25/00* | (2006.01) | |
| *A61B 18/00* | (2006.01) | |

(52) U.S. Cl.
CPC .... *A61M 25/0147* (2013.01); *A61M 25/0043* (2013.01); *A61M 25/0144* (2013.01);
(Continued)

(58) Field of Classification Search
CPC .......... A61M 25/0147; A61M 25/0043; A61M 25/0144; A61M 25/0138;
(Continued)

(56) References Cited

U.S. PATENT DOCUMENTS

| 4,719,924 A | 1/1988 | Crittenden et al. |
| 4,724,846 A | 2/1988 | Evans, III |
| | (Continued) | |

FOREIGN PATENT DOCUMENTS

| EP | 0435518 A1 | 7/1991 |
| WO | 97/42996 A1 | 11/1997 |
| | (Continued) | |

OTHER PUBLICATIONS

International Search Report and Written Opinion dated Jan. 7, 2016, for corresponding International Application No. PCT/CA2015/051049; International Filing Date: Oct. 20, 2015 consisting of 11-pages.

(Continued)

*Primary Examiner* — Sean P Dougherty
(74) *Attorney, Agent, or Firm* — Christopher & Weisberg, P.A.

(57) ABSTRACT

A device and system for providing a centered lumen within a catheter body. A coiled guide lumen (CGL) is composed of a length of wire forming a plurality of coils about the longitudinal axis of the CGL, the CGL including one or more first sections having a first diameter and one or more sections having a second diameter, the second diameter being greater than the first diameter, and a secondary guide lumen extending through the first sections. The CGL may include at least one pull wire extending through the secondary guide lumen and attached at the distal portion of the catheter body. A band may be coupled to an interior of the catheter body distal portion, each of the pull wires being coupled to the annular band. Alternatively, the system may further include a shim coupled to the band, each of the pulls wire being coupled to the shim.

15 Claims, 12 Drawing Sheets

(52) U.S. Cl.
CPC .......... *A61B 18/00* (2013.01); *A61M 25/0138* (2013.01); *A61M 2025/0059* (2013.01); *A61M 2025/0161* (2013.01)

(58) Field of Classification Search
CPC .. A61M 2025/0161; A61M 2025/0059; A61B 18/00
See application file for complete search history.

(56) References Cited

U.S. PATENT DOCUMENTS

| | | | |
|---|---|---|---|
| 4,917,666 A | 4/1990 | Solar et al. | |
| RE33,911 E | 5/1992 | Samson et al. | |
| 5,228,453 A | 7/1993 | Sepetka | |
| 5,306,252 A | 4/1994 | Yutori et al. | |
| 5,449,362 A | 9/1995 | Chaisson et al. | |
| 5,514,128 A | 5/1996 | Hillsman et al. | |
| 5,676,653 A | 10/1997 | Taylor et al. | |
| 5,746,701 A * | 5/1998 | Noone | A61M 25/09 600/585 |
| 5,766,160 A * | 6/1998 | Samson | A61B 17/12022 606/1 |
| 5,827,201 A | 10/1998 | Samson et al. | |
| 5,931,830 A | 8/1999 | Jacobsen et al. | |
| 6,017,319 A | 1/2000 | Jacobsen et al. | |
| 6,024,765 A * | 2/2000 | Wallace | A61B 17/12022 606/191 |
| 6,071,274 A * | 6/2000 | Thompson | A61B 18/1492 604/528 |
| 6,217,595 B1 * | 4/2001 | Shturman | A61B 17/320758 242/430 |
| 6,332,880 B1 * | 12/2001 | Yang | A61M 25/0043 604/528 |
| 6,356,791 B1 | 3/2002 | Westlund et al. | |
| 6,458,137 B1 * | 10/2002 | Klint | A61B 17/12022 606/108 |
| 6,526,979 B1 * | 3/2003 | Nikolchev | A61B 17/12022 128/830 |
| 6,537,248 B2 * | 3/2003 | Mulier | A61B 18/1477 604/114 |
| 6,893,421 B1 * | 5/2005 | Larson | A61M 25/0021 604/164.01 |
| 6,896,671 B2 * | 5/2005 | Vitullo | A61M 25/0043 604/524 |
| 7,150,723 B2 * | 12/2006 | Meguro | A61M 25/09033 604/96.01 |
| 7,848,788 B2 * | 12/2010 | Tulley | G01R 33/34053 324/318 |
| 7,880,578 B2 * | 2/2011 | Meinke | G01R 33/34007 242/430 |
| 7,918,870 B2 * | 4/2011 | Kugler | A61M 25/09 606/185 |
| 8,267,985 B2 * | 9/2012 | Garcia | A61B 17/12022 623/1.11 |
| 8,317,678 B2 * | 11/2012 | Frassica | A61B 1/00154 600/101 |
| 8,372,017 B2 | 2/2013 | Schiff et al. | |
| 8,403,867 B2 * | 3/2013 | Nowak, Jr. | A61M 25/09 600/585 |
| 8,535,345 B2 * | 9/2013 | Desai | A61B 17/12022 606/200 |
| 8,545,573 B2 * | 10/2013 | Matthews | A61B 17/12022 623/23.72 |
| 8,702,746 B2 * | 4/2014 | Tekulve | A61B 17/12022 606/200 |
| 8,715,441 B2 * | 5/2014 | Brustad | A61B 1/0055 156/143 |
| 8,764,727 B2 * | 7/2014 | Lentz | A61M 25/005 604/103.09 |
| 8,777,841 B2 * | 7/2014 | Frassica | A61B 1/00082 600/114 |
| 8,870,908 B2 * | 10/2014 | Labdag | A61B 17/12022 606/200 |
| 8,926,528 B2 * | 1/2015 | Govari | A61B 5/065 600/585 |
| 9,615,833 B2 * | 4/2017 | Suzuki | A61B 17/12031 |
| 9,839,766 B2 * | 12/2017 | Deac | A61M 25/0144 |
| 2004/0167442 A1 * | 8/2004 | Shireman | A61M 25/09 600/585 |
| 2005/0080357 A1 | 4/2005 | Eberhart et al. | |
| 2008/0004546 A1 | 1/2008 | Kato | |
| 2012/0123329 A1 | 5/2012 | Kato | |
| 2012/0165802 A1 | 6/2012 | Lalonde | |
| 2014/0052109 A1 * | 2/2014 | Organ | A61M 25/0147 604/528 |

FOREIGN PATENT DOCUMENTS

| | | |
|---|---|---|
| WO | 9742996 A1 | 11/1997 |
| WO | 2001/54761 A2 | 8/2001 |
| WO | 0154761 A2 | 8/2001 |
| WO | 2010/102105 A1 | 9/2010 |
| WO | 2012/116337 A1 | 8/2012 |

OTHER PUBLICATIONS

China National Intellectual Property Administration, Notice on the First Office Action and Search Report for corresponding Chinese Application No. 201580056631.8, 18 pages.
Supplementary European Search Report dated Apr. 11, 2018, for corresponding European Application No. 15853073.3; consisting of 2-pages.

* cited by examiner

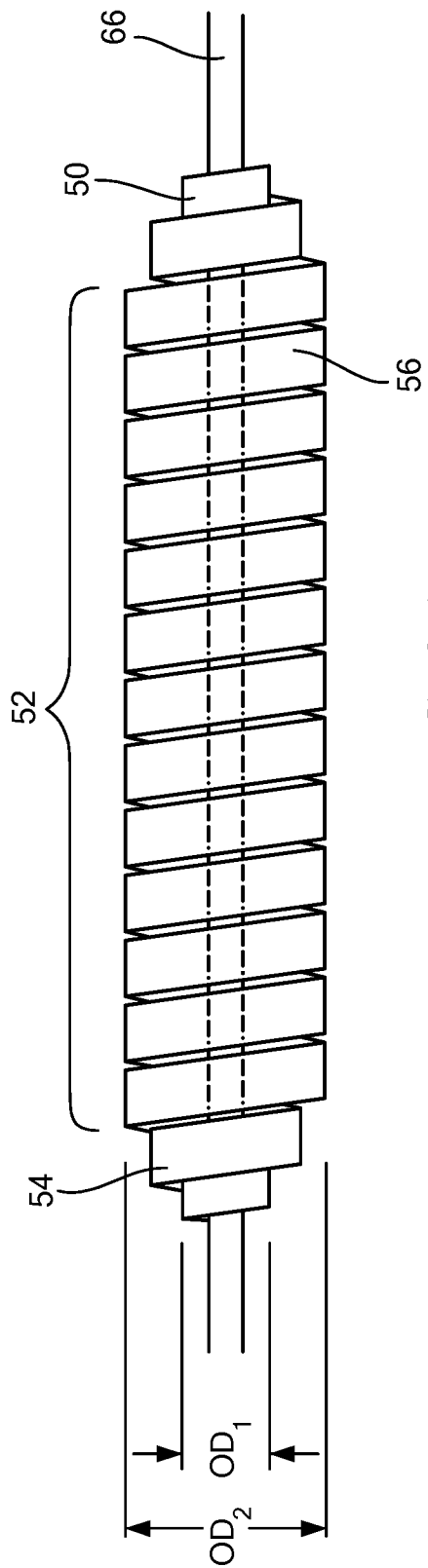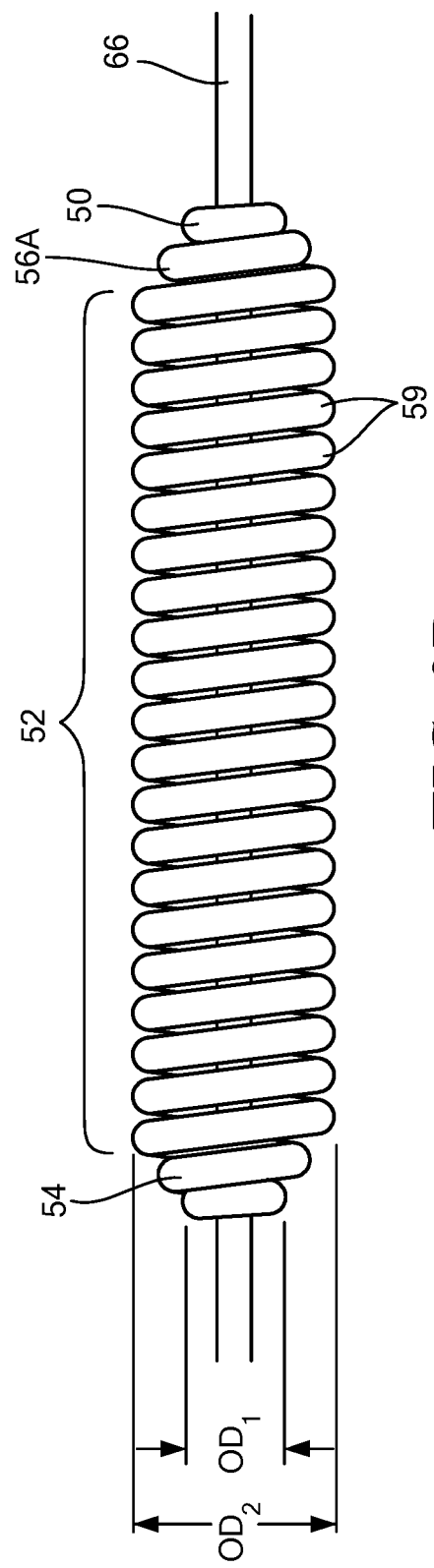
FIG. 3A
FIG. 3B

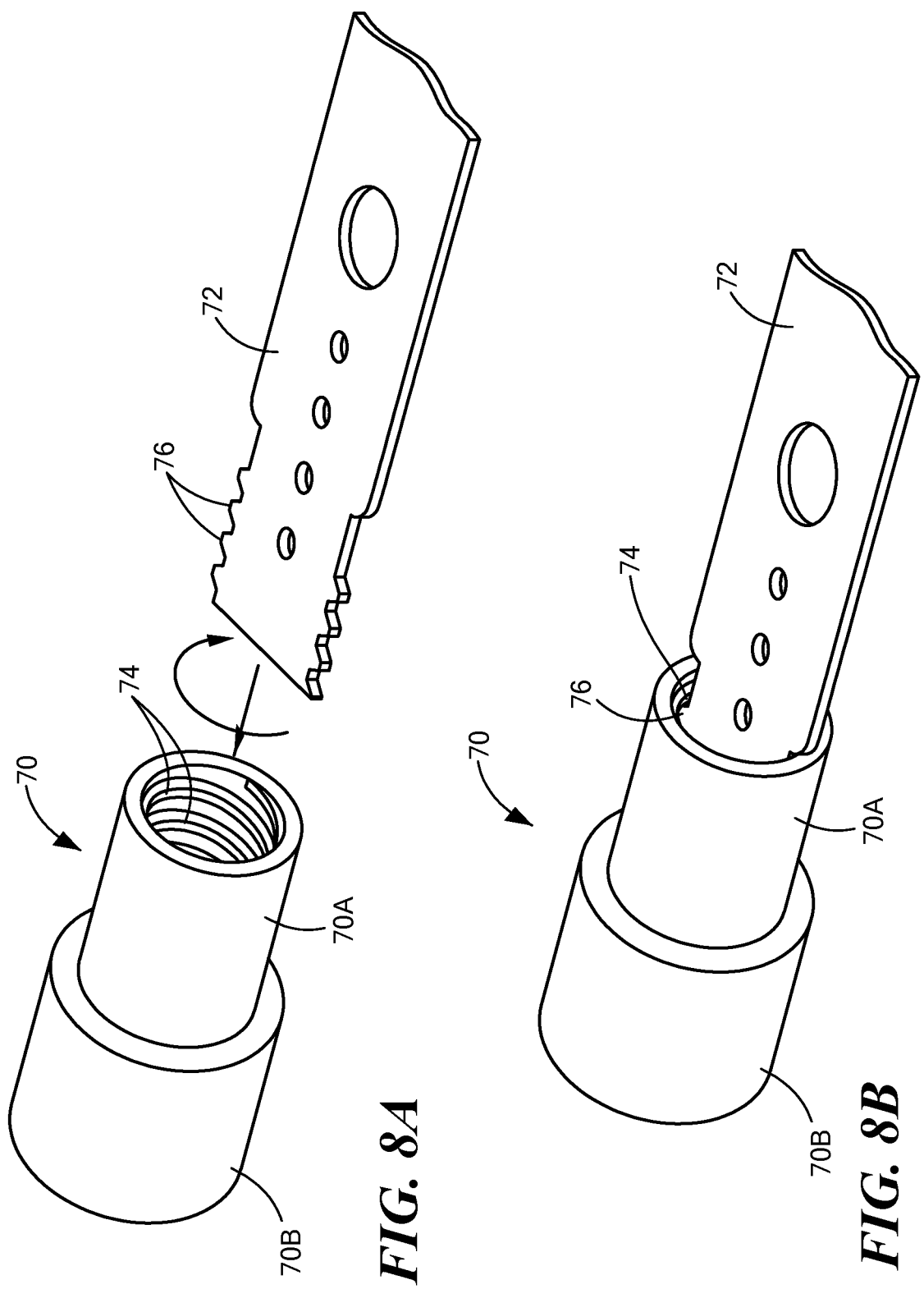

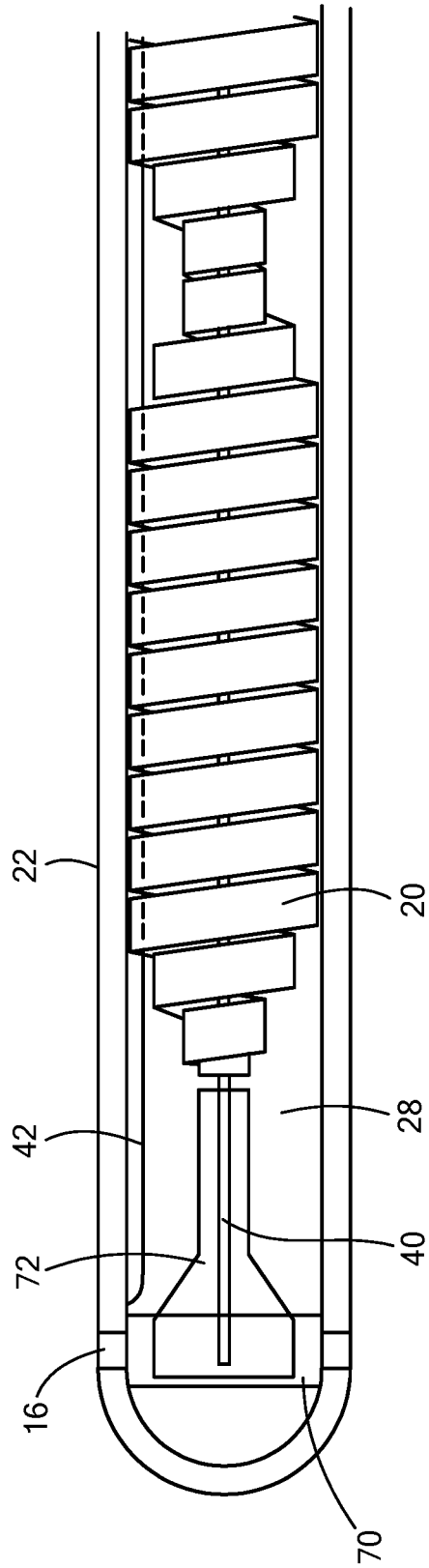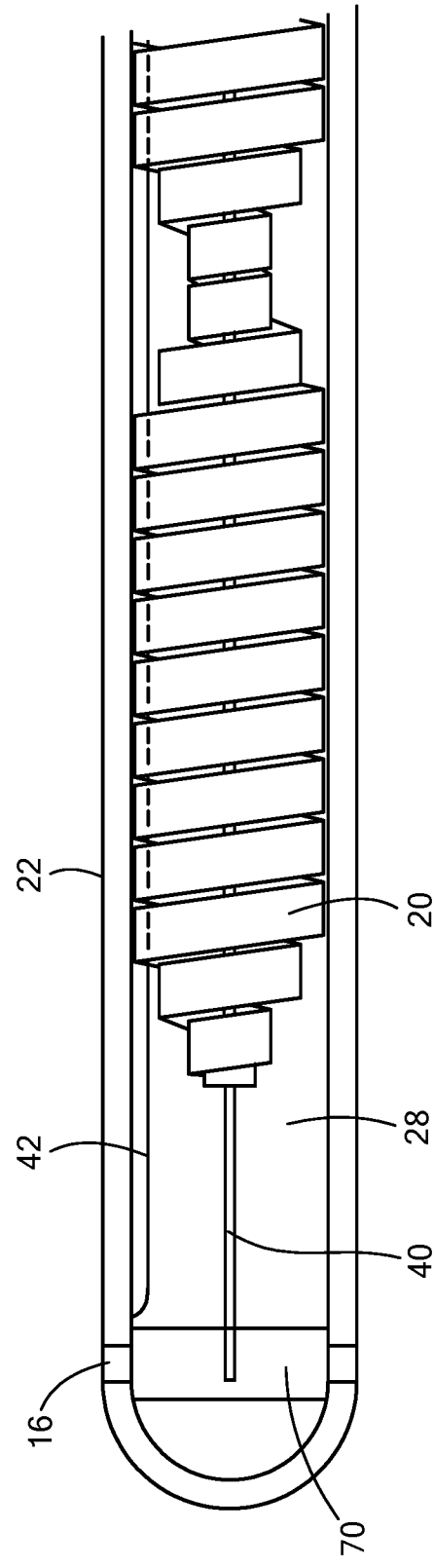

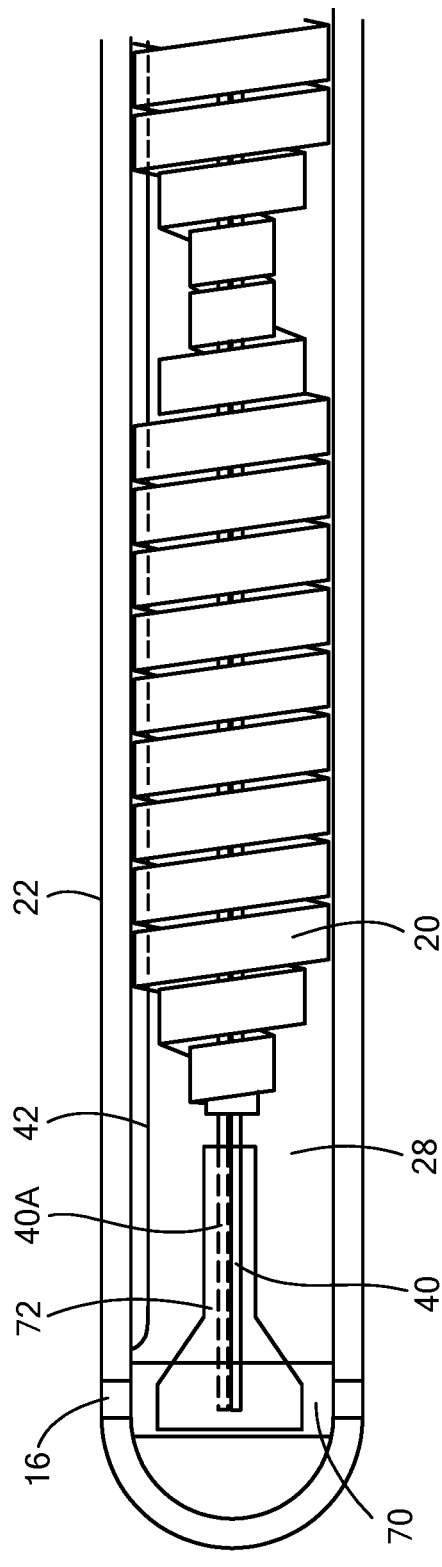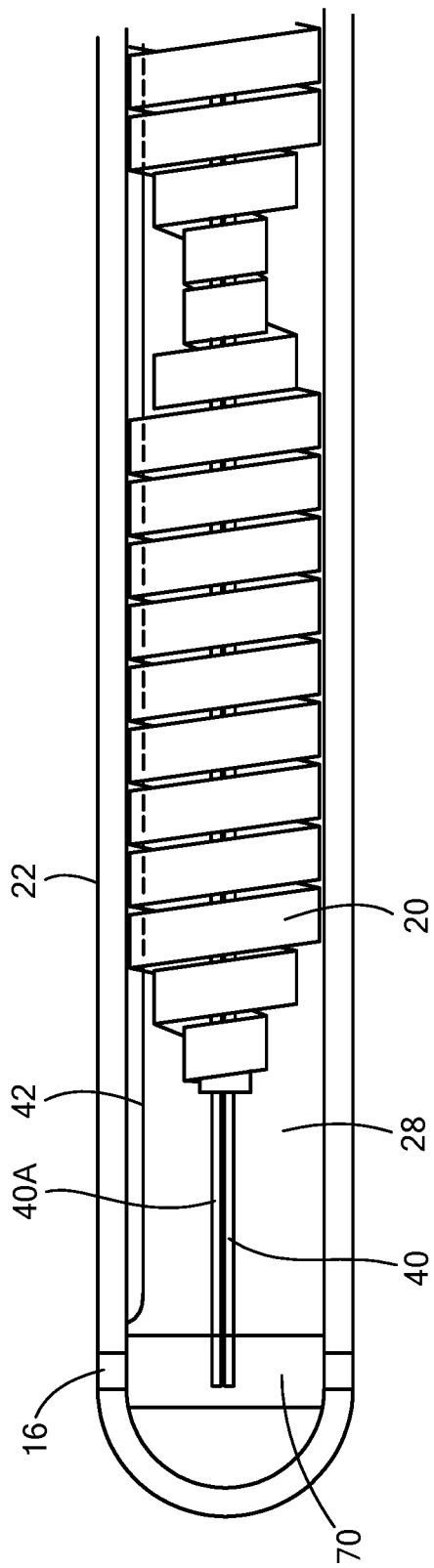

CENTERING COILED GUIDE

CROSS-REFERENCE TO RELATED APPLICATION

This application is a continuation of and claims priority to patent application Ser. No. 14/518,545, filed Oct. 20, 2014, entitled CENTERING COILED GUIDE, the entirety of which is incorporated herein by reference.

STATEMENT REGARDING FEDERALLY SPONSORED RESEARCH OR DEVELOPMENT n/a

FIELD OF THE INVENTION

The present invention relates to a method, device, and system for providing a lumen within a catheter body. The present invention further relates to a method, device, and system for providing a lumen within a catheter body that preserves the flexibility of the catheter body and that is centered within the catheter body.

BACKGROUND OF THE INVENTION

Catheters are medical devices commonly used for a variety of medical procedures and purposes, including cardiac ablation and treatment techniques. Typically, a catheter used for endocardial procedures include an elongate, flexible body that extends from the device handle. Not only is the flexible body sized to be positioned within the patient's vasculature, but the flexible body must also be flexible enough to be navigated through the patient's body and steerable enough to be positioned at the target treatment site. Therefore, the elongate body must contain the necessary device components, such as pull wires, shims, fluid delivery and recovery lumens, electrical wires, and others, depending on the type of the device. Consequently, an elongate body may need to include a plurality of lumens or channels therein to accommodate all these elements and, in many cases, keep them isolated from each other (for example, some components may need to be mechanically, fluidly, thermally, and/or electrically isolated from others).

Not surprisingly, these features may significantly add to the manufacturing cost of the catheter body and the device as a whole. Each type of catheter body must be designed and manufactured independently, with very few, if any, designs being a one-size-fits-all design. Additionally, including a plurality of lumens within the catheter body may not only take up valuable and limited space within the body, but may also decrease the overall flexibility and steerability of the body.

Therefore, it is desirable to provide a catheter body that includes a central lumen that can be used to center certain components, such as pull wires and guidewire lumens, and that also remains flexible. It is further desired to provide a device that can be incorporated into a simply manufactured catheter body (for example, an extruded tube) to provide these benefits and to reduce manufacturing costs.

SUMMARY OF THE INVENTION

The present invention advantageously provides a method, device, and system for providing a centered lumen within a catheter body. The present invention further relates to a method, device, and system for providing a lumen within a catheter body that preserves the flexibility of the catheter body and that is centered within the catheter body. A coiled guide lumen defining a longitudinal axis may include a length of wire forming a plurality of coils about the longitudinal axis, the plurality of coils having a variable outer diameter, the coiled guide being sized to be contained within a catheter elongate body, the coiled guide extending from a proximal portion of the catheter elongate body to a distal portion of the catheter elongate body. The plurality of coils may include a plurality of first sections each having a first outer diameter and a plurality of second sections each having a second outer diameter, the second diameter being greater than the first diameter. Each of the plurality of first sections may have a first length and each of the plurality of second sections may have a second length, the second length being greater than the first length. For example, each of the plurality of first sections may include between one and five coils. Alternatively, the first length may be greater than the second length. For example, each of the plurality of second sections may include between one and five coils. The plurality of coils may further include a transition section on each side of each of the plurality of second sections. Additionally, the coiled guide lumen may include a first end and a second end, with a first section being at each of the first end and second end. The wire may have a flat or round cross section. The coiled guide lumen may further include a secondary guide lumen that is passed through coils in the plurality of first sections, such that the secondary guide lumen and the coiled guide lumen are coaxial. The secondary guide lumen may be composed of a material having a low coefficient of friction, such as polyimide. The coiled guide lumen may further include one or more pull wires extending through plurality of first sections.

A system having a centered lumen may include: a coiled guide lumen defining a longitudinal axis, the coiled guide lumen being composed of a length of wire forming a plurality of coils about the longitudinal axis, the coiled guide lumen including one or more first sections having a first diameter and one or more sections having a second diameter, the second diameter being greater than the first diameter; an elongate body including a proximal portion and a distal portion, the coiled guide lumen being within the elongate body and extending between the proximal portion and the distal portion; and a secondary guide lumen extending through the one or more first sections. The system may further include one or more pull wires extending through the secondary guide lumen. The system may further include a band coupled to an interior of the distal portion of the elongate body, and the proximal portion of the elongate body may be coupled to a handle. Each of the one or more pull wires may have a proximal portion and a distal portion, the proximal portion of the one or more pull wires being in mechanical communication with the handle and the distal portion of each of the one or more pull wires being coupled to the band. Alternatively, the system may further include a shim coupled to the band and the distal portion of each of the one or more pull wires may be coupled to the shim.

A system having a centered lumen may include: a coiled guide lumen defining a longitudinal axis, the coiled guide lumen being composed of a length of wire forming a plurality of coils about the longitudinal axis, the coiled guide lumen including one or more first sections having a first diameter and one or more sections having a second diameter, the second diameter being greater than the first diameter; an elongate body including a proximal portion and a distal portion, the coiled guide lumen being within the elongate body and extending between the proximal portion and the distal portion; a secondary guide lumen extending through the one or more first sections; and at least one pull wire extending through the secondary guide lumen and being attached at the distal portion of the elongate body. The system may further include an annular band coupled to an interior of the distal portion of the elongate body, and each of the at least one pull wire may be coupled to the annular band. Alternatively, the system may further include a flexible shim coupled to the annular band, and each of the at least one pull wire may be coupled to the flexible shim.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3A shows a side view of a section of the first embodiment of the coiled guide, the coiled guide being formed from a flat wire;

FIG. 3B shows a side view of the first embodiment of the coiled guide, the coiled guide being formed from a round wire;

FIGS. 8A and 8B show a first and second view of an attachment between a shim and a threaded element;

FIG. 9 shows a cross-sectional view of a coiled guide and a first embodiment of a single-deflection steering mechanism within a catheter body;

FIG. 10 shows a cross-sectional view of a coiled guide and a second embodiment of a single-deflection steering mechanism within a catheter body;

FIG. 11 shows a cross-sectional view of a coiled guide and a first embodiment of a dual-deflection steering mechanism within a catheter body;

FIG. 12 shows a cross-sectional view of a coiled guide and a second embodiment of a dual-deflection steering mechanism within a catheter body

DETAILED DESCRIPTION OF THE INVENTION

Figure 1:
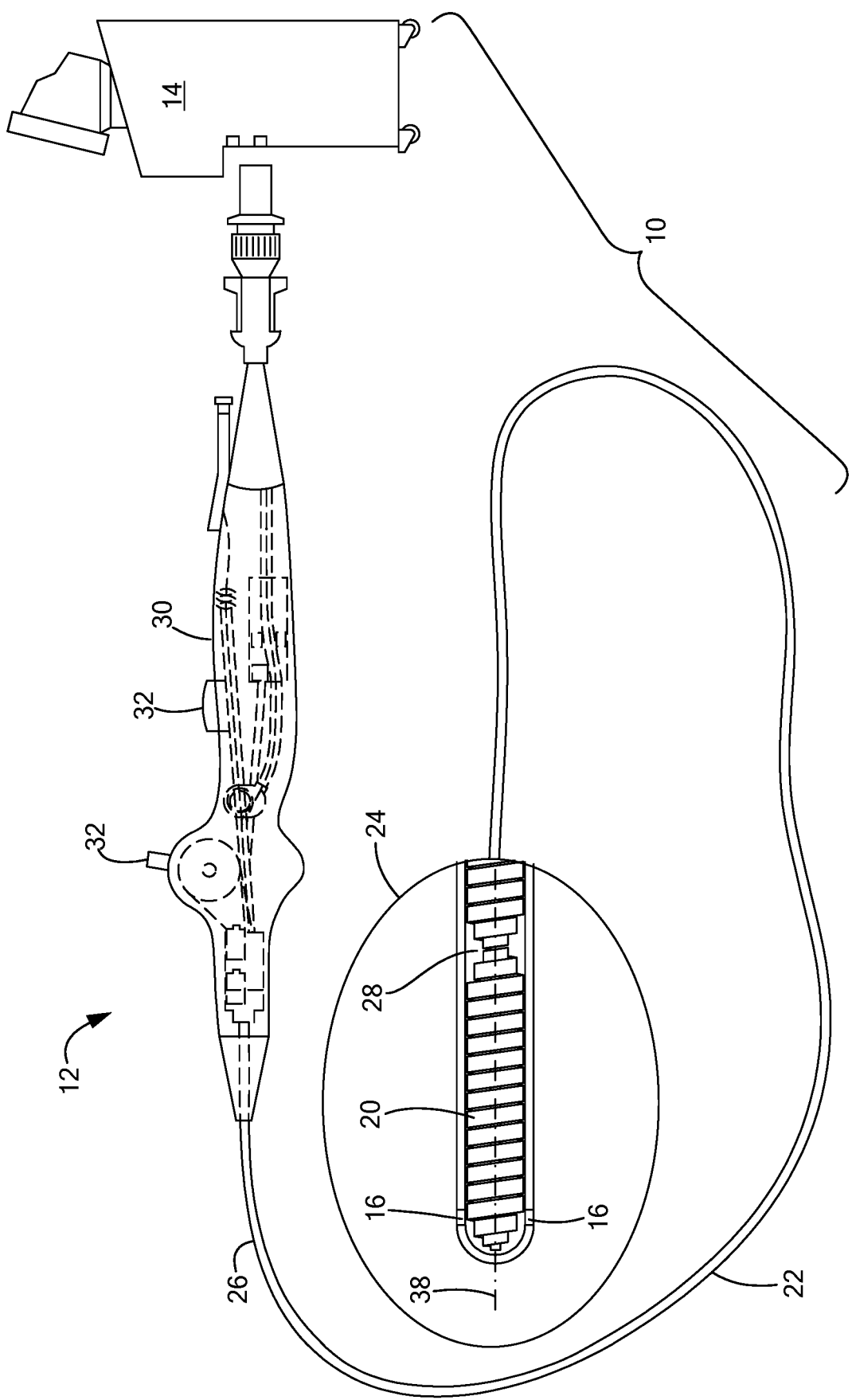
FIG. 1 shows an exemplary medical system that includes a treatment catheter including a coiled guide.

Referring now to the drawing figures in which like reference designations refer to like elements, an exemplary medical system that includes a treatment catheter including a coiled guide is shown in FIG. 1 and is generally designated as "10." The system 10 generally includes a catheter 12 that may be coupled to a control unit 14 or operating console. The catheter 12 may be configured to interact with tissue, such as with one or more electrodes 16. For example, the catheter 12 may be a treatment catheter that is configured thermally treat tissue. The catheter 12 may also include a coiled guide 20 (which may also be referred to as a "coiled guide lumen 20") extending within and along the length of the catheter, as shown and described in more detail in FIGS. 2-13.

The catheter 12 may include an elongate body 22 having a distal portion 24 and a proximal portion 26, and defining a lumen 28 therebetween. The proximal portion 26 of the elongate body 22 may be coupled to or otherwise in mechanical, electrical, and/or fluid communication with a handle 30, which may be, in turn, coupled to or otherwise in mechanical, electrical, and/or fluid communication with the control unit 14. The control unit 14 may include one or more energy sources (such as radiofrequency or laser) and/or cryogenic fluid for cryotreatment, vacuums, fluid reservoirs, computers, user input devices, displays, and processors. The handle 30 may include one or more steering controls 32 that are in mechanical communication with the distal portion 24 of catheter 12. The one or more steering controls 32 may be used, for example, to navigate the catheter 12 through the patient's vasculature and/or to modify the size, configuration, and/or operation of a treatment element or assembly at the distal portion 24.

Figure 13:
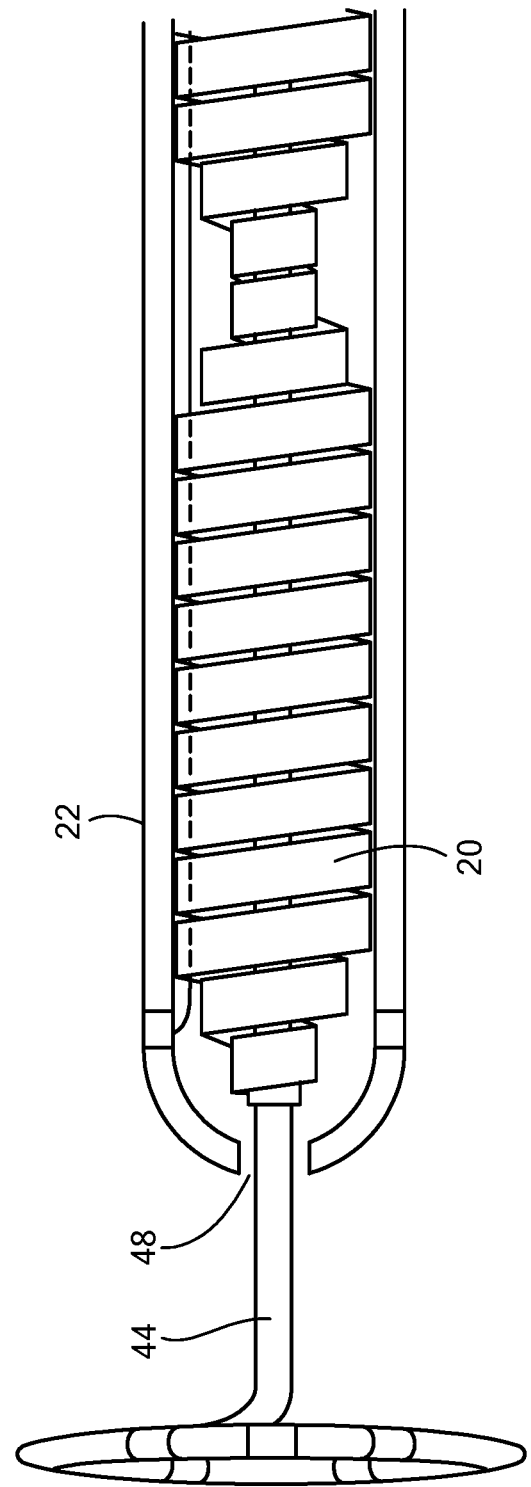
FIG. 13 shows a cross-sectional view of a coiled guide and a second embodiment of a dual-deflection steering mechanism within a catheter body, with a secondary medical device extending through the coiled guide.

The coiled guide 20 may define a longitudinal axis 38 and may be located within the elongate body lumen 28 and may extend from the proximal portion 26 to the distal portion 24 of the elongate body 22. The coiled guide 20 may be affixed to an inner surface of the elongate body 22, for example, by adhesive or chemical or thermal bonding. Alternatively, the coiled guide 20 may not be affixed within the elongate body 22. In this configuration, the catheter 12 may include a stopper at the proximal end of the elongate body 22 (not shown). In use, the coiled guide 20 may provide one or more channels or lumens along the length of the elongate body 22 for device components, such as pull wires 40, electrical wires 42, secondary medical devices 44 (such as a mapping catheter, as shown in FIG. 13), or the like. The distal end of the elongate body 22 may include an opening 48 through which a secondary medical device 44 or other component may exit the elongate body 22. For example, a mapping catheter 44 may extend out of the elongate body 22 and toward a target mapping or treatment site.

Referring now to FIGS. 2A-13, the coiled guide 20 is shown in greater detail. Referring specifically to FIGS. 2A-5, a first embodiment of the coiled guide 20 is shown. The coiled guide 20 may include a variable outer diameter, with one or more sections 50 having a first outer diameter $OD_1$ and one or more sections 52 having a second outer diameter $OD_2$, with the second outer diameter $OD_2$ being greater than the first outer diameter $OD_1$. Further, there optionally may be a transition section 54 on either side of the larger-diameter sections 52 that each includes a decreasing outer diameter (that is, an outer diameter that transitions from the second outer diameter $OD_2$ to the first outer diameter $OD_1$). The transition section 54 may include as few as one coil, in which case the diameter of the transition section coil may be greater than the first outer diameter $OD_1$ but less than the second outer diameter $OD_2$). Each of the smaller-diameter sections 50 may include several coils or may include as few as one coil, with each coil being a wrap of wire 56 about 360° (±15°) of the longitudinal axis 38. As a non-limiting example, each of the smaller-diameter sections 50 may include between one and five coils, inclusive, whereas each of the larger-diameter sections 52 may include five or more coils. Each end 58 of the coiled guide 20 may include at least one terminal coil 60 that has an outer diameter that is the same or approximately the same as the first outer diameter $OD_1$. Although referred to as a "wire," the coiled guide 20 may be formed from any deformable material that can be coiled about a longitudinal axis and maintain its shape. For example, the coiled guide 20 may be made from an elongate flat strip of metal. Further, to enhance flexibility, the wire 56 may be wound such that there is a small gap between adjacent coils. The width of the gap may be chosen based on the device in which the coiled guide 20 is used and/or the procedure in which the device is used.

Figure 5:
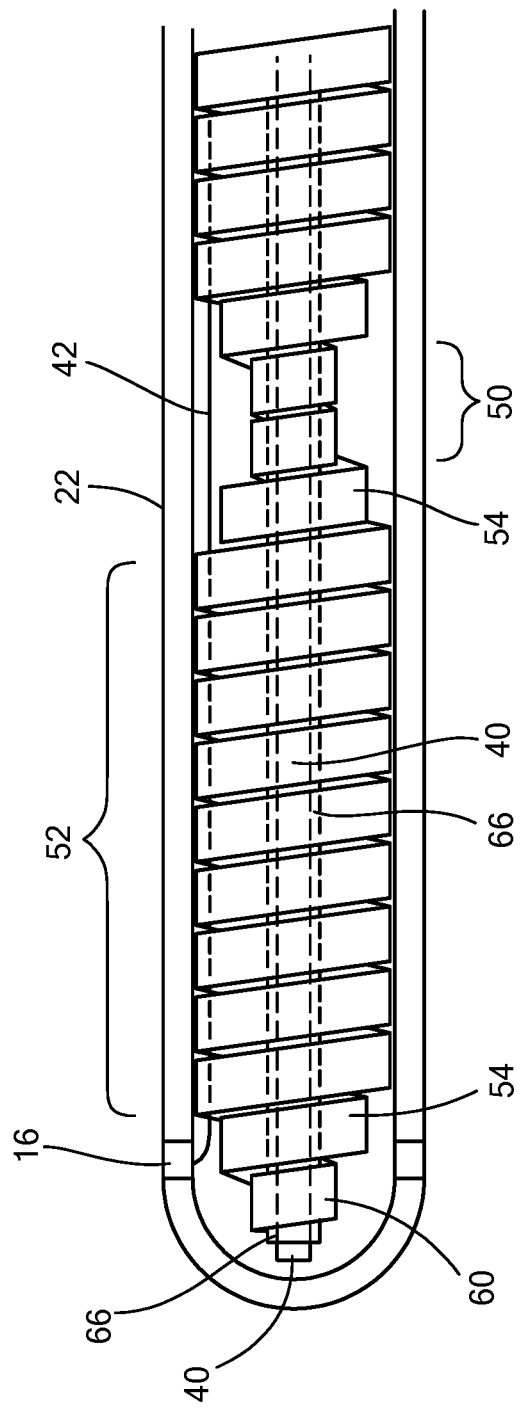
FIG. 5 shows a side view of the first embodiment of a coiled guide within a catheter body.
Figure 7:
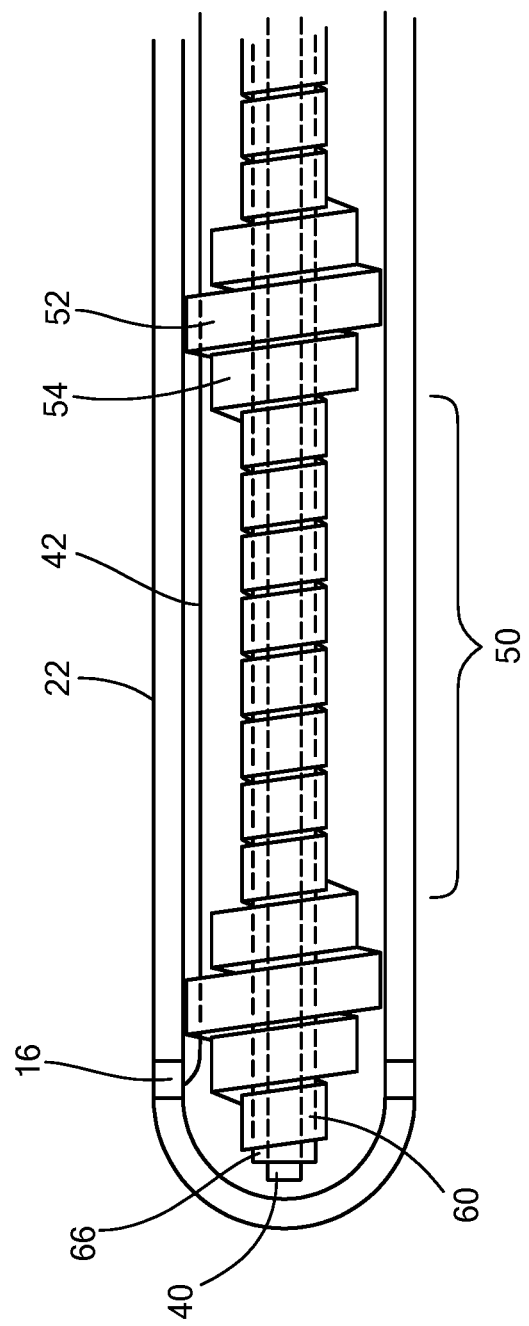
FIG. 7 shows a side view of the second embodiment of a coiled guide within a catheter body.

Optionally, a secondary guide lumen 66 may be inserted through the coiled guide 20, as shown in FIGS. 3A and 3B. For simplicity, a single unit of coiled guide 20 is shown (that is, one length of a larger-diameter portion 52, with a transition coil 54 and a smaller-diameter coil 50 on either side). The secondary guide lumen 66 may be an elongate tube that is made of a biocompatible and has a low coefficient of friction (for example, $\mu \leq 0.5$), such as polyimide. Additionally, the secondary guide lumen 66 may be sized to be passed through the coils of the smaller-diameter sections 50. As a non-limiting example, one or more pull wires 40 (as shown in FIGS. 5 and 7) and/or a secondary medical device 44 (as shown in FIG. 13) may be passed through the secondary guide lumen 66. The coiled guide 20 is configured such that the secondary guide lumen 66 and/or any other components passed through the smaller-diameter sections 50 may be centered within the elongate body 22. This may facilitate accurate steering using the one or more pull wires 40 and/or precise placement of a secondary medical device 44 at the treatment site. Further, the low-friction material of the secondary guide lumen 66 may allow the internal components and/or a secondary medical device 44 to slide freely within the secondary guide lumen 66. The Still further, other device components may be passed through the larger-diameter sections 52, such as electrical wires 42 and/or fluid lumens (not shown). Thus, the larger-diameter sections 52 may also provide lumen functionality, similar to the smaller-diameter sections 50. However, the device components passed through the larger-diameter sections 52 may not be centered within the elongate body 22.

Figure 4B:
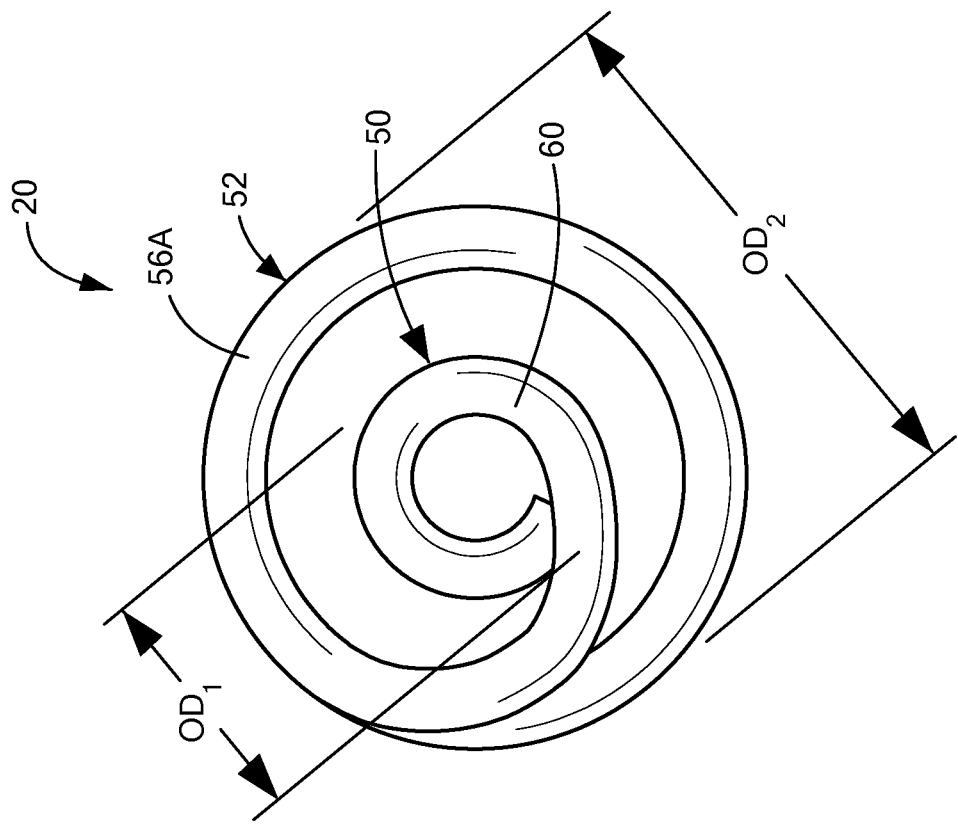
FIG. 4B shows a close-up end view of the first embodiment of the coiled guide, the coiled guide being formed from a round wire.
Figure 4A:
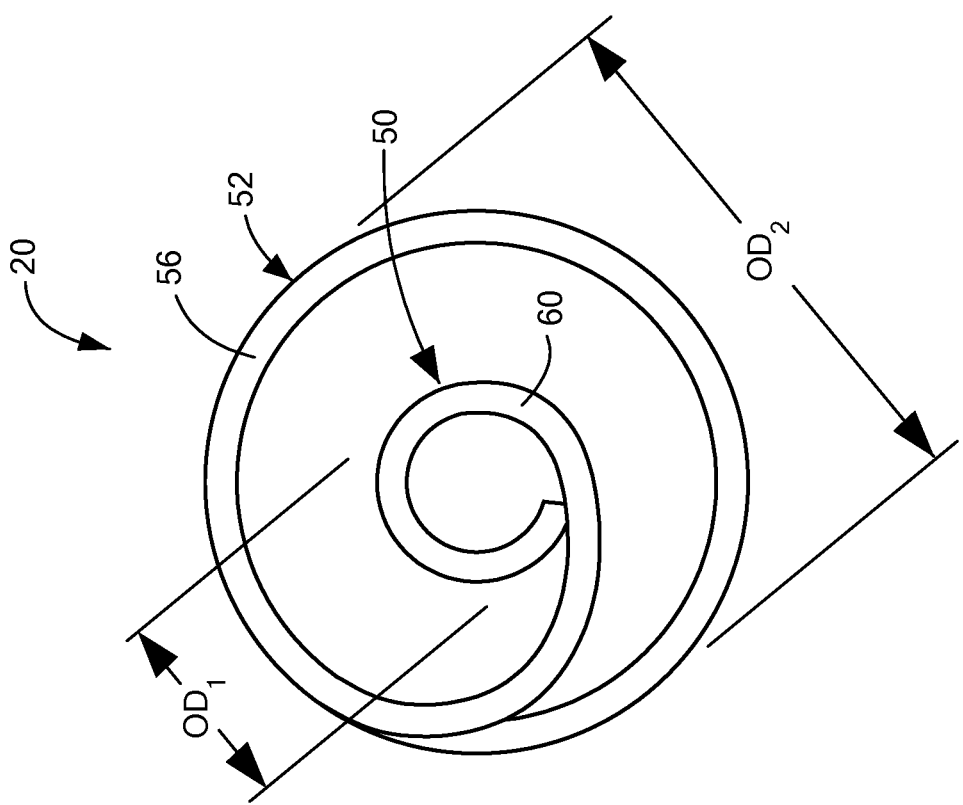
FIG. 4A shows a close-up end view of the first embodiment of the coiled guide, the coiled guide being formed from a flat wire.

The variable diameter of the coiled guide 20 can be seen, for example, in FIGS. 4A and 4B. The outer diameters $OD_1$, $OD_2$ may be any diameters that are suitable for the device in which the coiled guide 20 is used and/or for the internal components of the device and the way in which the device is steered and operated.

Figure 2A:
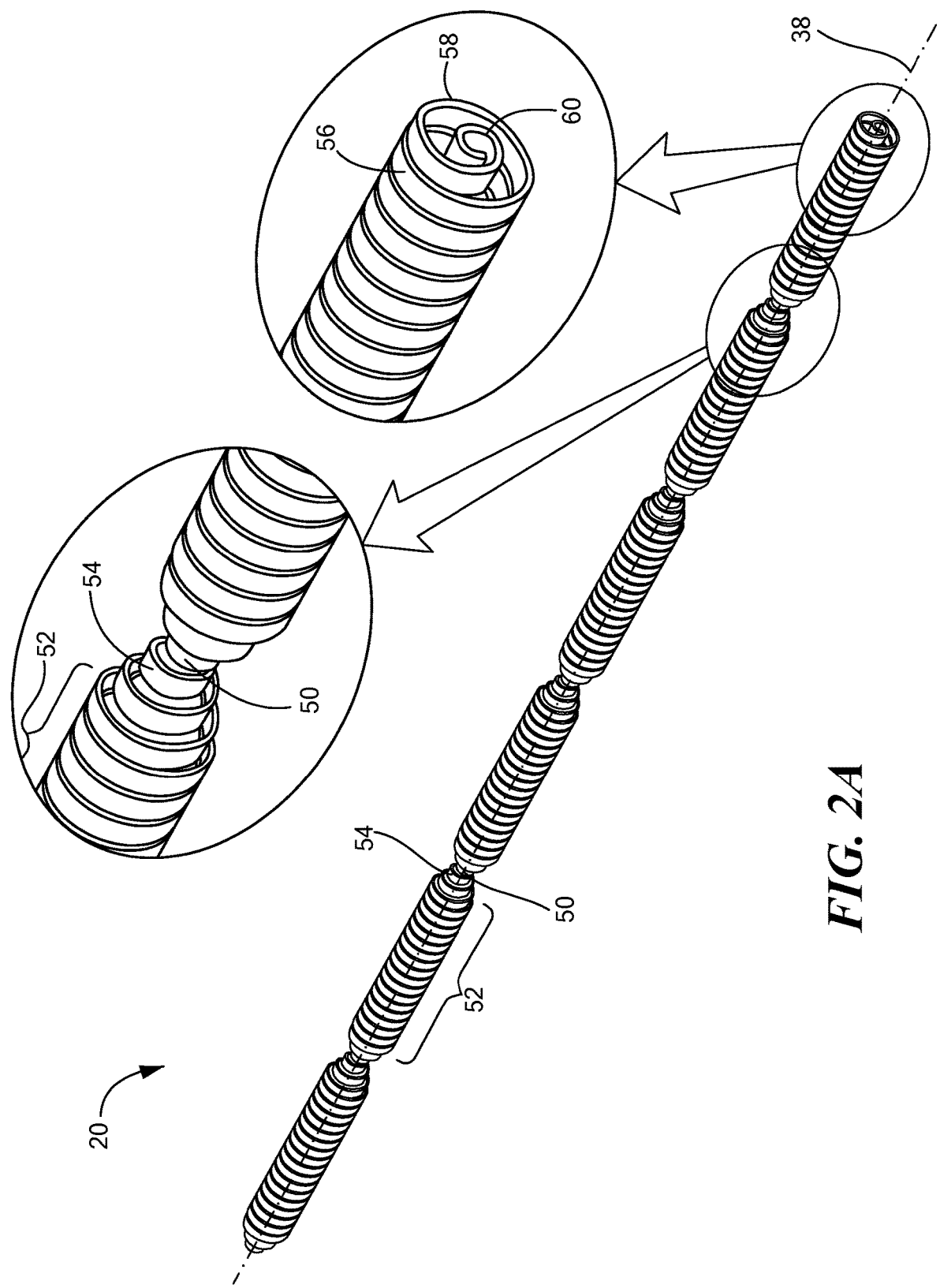
FIG. 2A shows a perspective view of a first embodiment of a coiled guide, the coiled guide being formed from a flat wire.
Figure 2B:
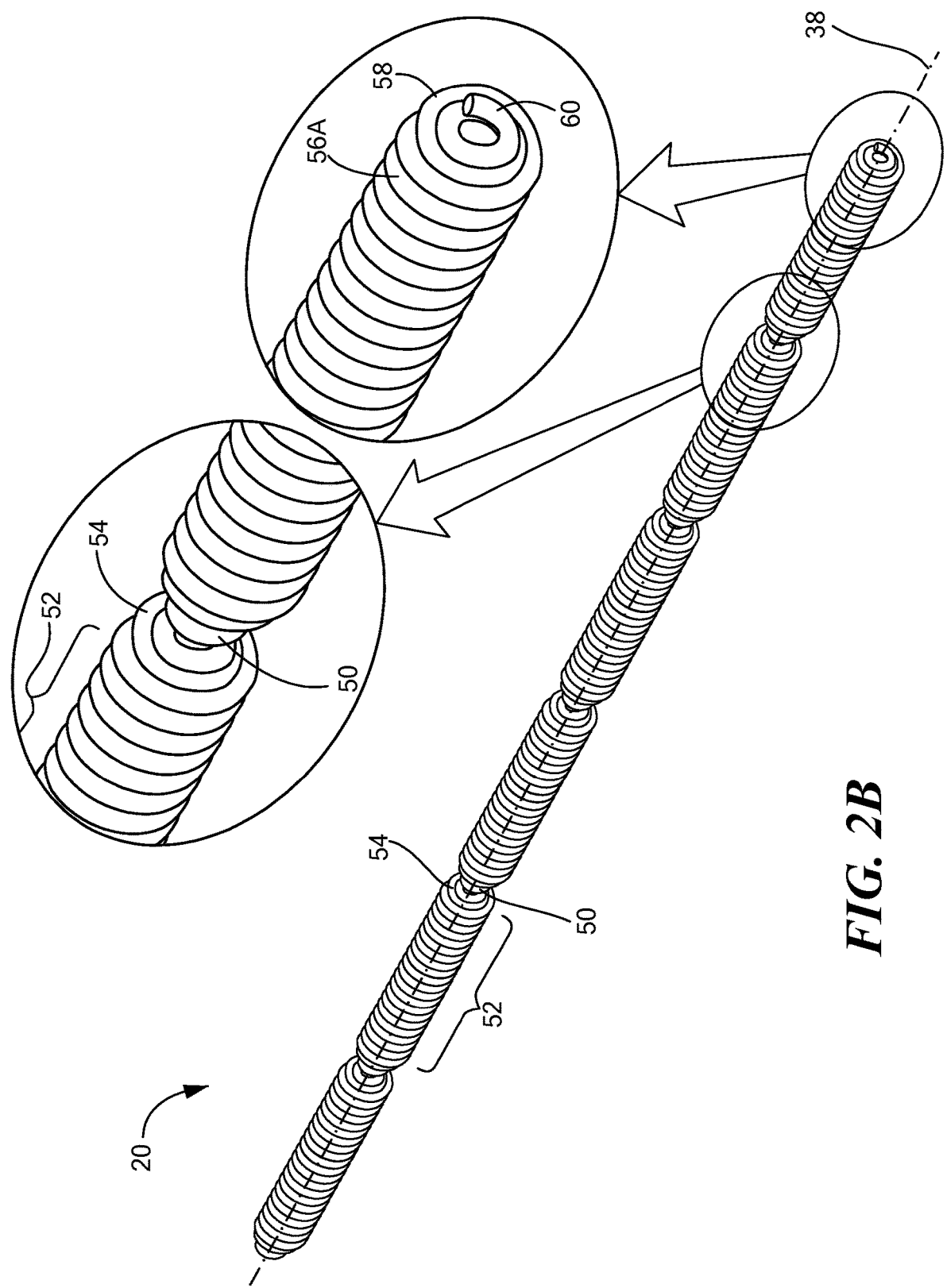
FIG. 2B shows a perspective view of the first embodiment of the coiled guide, the coiled guide being formed from a round wire.

The coiled guide 20 shown in FIGS. 2A, 3A, and 4A may be made from a flat wire 56, whereas the coiled guide 20 shown in FIGS. 2B, 3B, and 4B may be made from a round wire 56A. Otherwise, the coiled guide 20 shown in FIGS. 2B, 3B, and 4B may include the same features as the coiled guide 20 shown in FIGS. 2A, 3A, and 4A.

Figure 6:
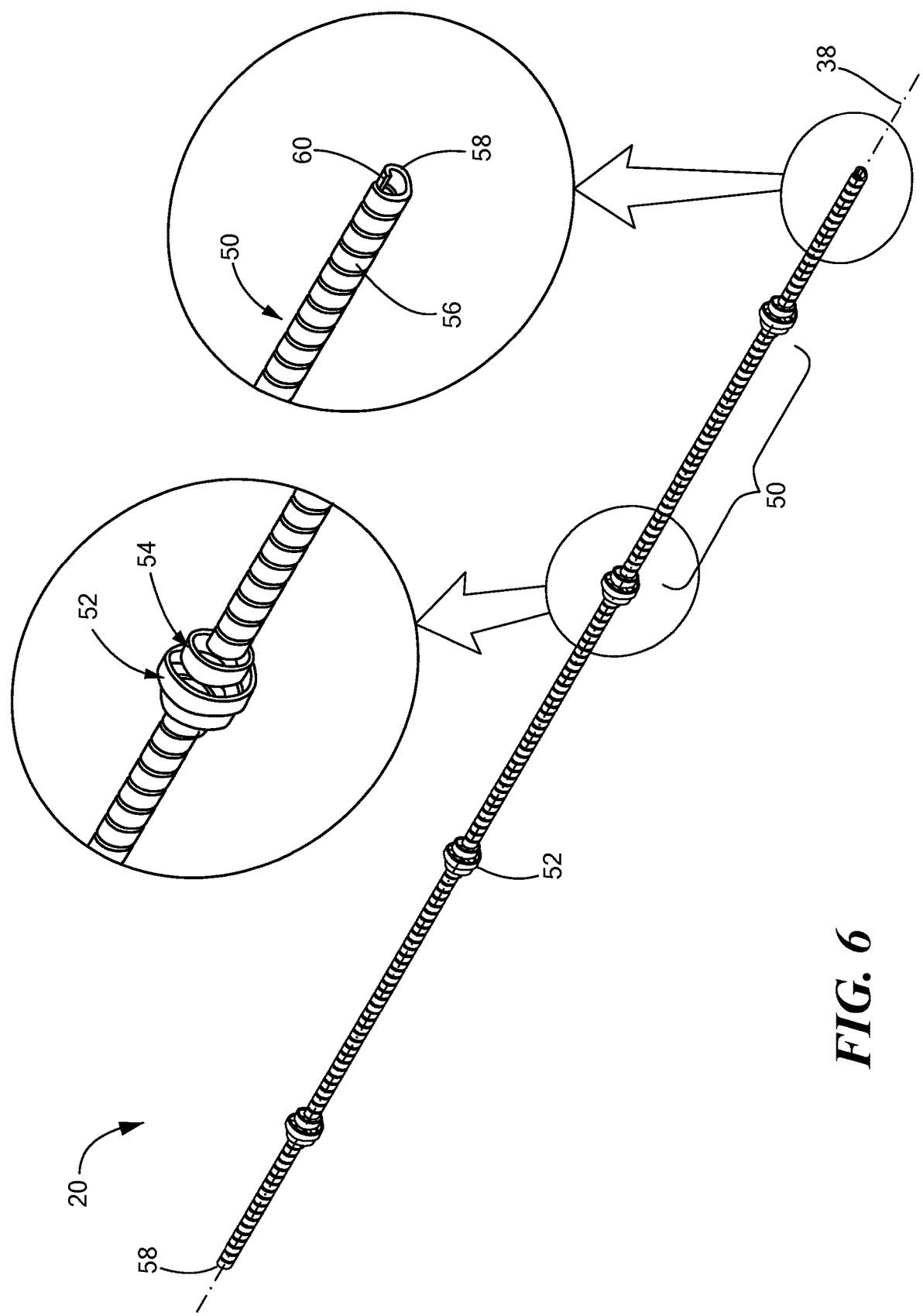
FIG. 6 shows a perspective view of a second embodiment of a coiled guide.

Referring now to FIGS. 6 and 7, a second embodiment of the coiled guide 20 is shown. The coiled guide 20 of FIG. 6 may have the same functionality as the first embodiment of the coiled guide 20 shown in FIGS. 2A-5. However, each of the smaller-diameter sections 50 may have a length $L_1$ that is greater than the length $L_2$ of each of the larger-diameter sections 52. In contrast, the first embodiment of the coiled guide 20 may include smaller diameter sections 50 that each has a length $L_1$ that is less than the length $L_2$ of each of the larger-diameter sections 52. The larger-diameter sections 52 and the transition sections 54 may each include as few as one coil, whereas the smaller-diameter sections 50 may each include a plurality of coils. As a non-limiting example, each of the larger-diameter sections 52 may include between one and five coils, inclusive, whereas each of the smaller-diameter sections 50 may include five or more coils. The embodiment shown in FIG. 6 may be desirable when it is important that a high degree of flexibility be maintained in the elongate body 22. Like the first coiled guide 20 embodiment shown in FIGS. 2A-5, the second coiled guide 20 embodiment shown in FIG. 5 may alternatively be formed from a flat wire 56 or a round wire 56A. Further, as shown in FIG. 7, a secondary guide lumen 66 and/or other device components may be passed through the coiled guide 20 as shown and described in FIGS. 2A-5.

Referring now to FIGS. 8A-12, non-limiting embodiments of a steering mechanism are shown. FIGS. 8A and 8B show a means of attachment between a threaded assembly 70 in the distal portion 24 of the elongate body 22 to which a shim 72 may be coupled. For example, the threaded element 70 may be, may define, or may include a threaded annular band. The threaded element 70 is shown in FIGS. 8A and 8B as an assembly having a proximal portion 70A and a distal portion 70B. The proximal portion 70A may be hollow and may include threading 74 on an inner surface, and the distal portion 70B may be hollow or at least partially hollow and at least a portion of the inner surface may also include threading 74. That is, the threading 74 may extend entirely or partially within the distal portion 70B. The threaded element 70 is shown in FIGS. 9-12 as an annular band. The threaded element 70 may be coupled to the interior of the elongate body 22 so that it does not move within the elongate body 22 when a pull force is exerted on the pull wire 40. Further, the threaded element 70 may be composed of rigid material, such as metal or plastic. The shim 72 may be a flattened plate that includes threading 76 on two of its edges, the threading 76 being rotatably matable with (that is, able to be screwed into) the threading 74 within the threaded element 70. Further, the shim 72 may be dimensioned such that the shim 72 is securely attached within the threaded element 70 when the shim 72 is screwed in. The shim 72 may be composed of a flexible and resilient material, such as thin layer of metal or plastic.

FIGS. 9 and 10 each show a steering method embodiment in which the distal portion 24 of the elongate body 22 may be deflected in a single direction, and FIGS. 11 and 12 each show a steering method embodiment in which the distal portion 24 of the elongate body 22 may be deflected in two directions. The pull wire 40 may be attached to, such as welded or bonded to, a surface of the shim 72 so that a pull force exerted on the pull wire 40 may cause the shim 72, and therefore the distal portion 24 of the elongate body 22, to deflect toward the side of the shim to which the pull wire 40 is attached. Thus, the elongate body 22 may be deflectable in a single direction. The shim 72 may have an at least substantially continuous width, as shown in FIGS. 8A and 8B, or it may be tapered as shown in FIGS. 9 and 11, with the distal end being wide enough to be screwed into the threaded element 70. The narrower diameter of the proximal portion of the shim 72 may enhance flexibility of the shim 72.

In the alternative embodiment shown in FIG. 10, the pull wire 40 may be attached directly to the band 70, but may produce the same one-directional deflection as the embodiment shown in FIG. 9.

The embodiment shown in FIG. 11 is similar to the embodiment shown in FIG. 9, except the catheter 12 may include two pull wires 40, 40A attached to the shim 72. For example, one pull wire 40 may be attached to one face of the shim 72 and a second pull wire 40A may be attached to the opposite face of the shim 72. A pull force exerted on the pull wire 40 may cause the shim 72, and therefore the distal portion 24 of the elongate body 22, to deflect toward the side of the shim 72 to which the pull wire 40 is attached. Similarly, a pull force exerted on the pull wire 40A may cause the shim 72, and therefore the distal portion 24 of the elongate body 22, to deflect toward the side of the shim 72 to which the pull wire 40A is attached. Thus, the elongate body 22 may be deflectable in two directions.

In the alternative embodiment shown in FIG. 12, the pull wires 40, 40A may be attached directly to the band 70, but may produce the same dual-directional deflection as the embodiment shown in FIG. 11.

When the coiled guide 20 is used in a catheter, the elongate body 22 of the catheter may be manufactured in a simple, efficient, and cost-effective process. For example, instead of complicated extrusion, a plurality of elongate bodies 22 may be manufactured in a single, continuous extruded tube having a single lumen. The continuous extruded tube may then be cut into a plurality of working lengths, each length becoming a catheter elongate body. After extrusion, one or more coiled guides 20 may be inserted into an elongate body to provide the elongate body with one or more lumens through which various device components and/or secondary medical devices may be passed.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A coiled guide lumen defining a longitudinal axis, the coiled guide lumen comprising:
   at least one first coil having a first outer diameter and a first length along the longitudinal axis;
   at least one second coil distal to the at least one first coil and at least one third coil proximal to the at least one first coil, each of the at least one second coil and the at least one third coil having a second outer diameter, the second outer diameter being less than the first outer diameter, the at least one second coil and the at least on third coil each having a second length along the longitudinal axis, the second length being less than the first length;
   a plurality of fourth coils distal to the at least one second coil and a plurality of fifth coils proximal to the at least one third coil, each of the plurality of fourth coils and the plurality of fifth coils having a third outer diameter, the third outer diameter being less than the second outer diameter, the plurality of fourth coils and the plurality of fifth coils each having a third length along the longitudinal axis, the third length being less than the first length and equal to or less than the second length;
   a secondary guide lumen that is passed through the plurality of forth coils and the plurality of fifth coils, such that the secondary guide lumen and the coiled guide lumen are coaxial, the secondary guide lumen being composed of polyimide, a material having a low coefficient of friction; and
   one or more pull wires extending through the secondary guide lumen.

2. The coiled guide lumen of claim 1, wherein the at least one first coil is one first coil.

3. The coiled guide lumen of claim 1, wherein the at least one first coil includes at most five first coils.

4. The coiled guide lumen of claim 1, wherein the at least one second coil is one second coil and the at least one third coil is one third coil.

5. The coiled guide lumen of claim 1, wherein the at least one second coil includes at most five coils.

6. The coiled guide lumen of claim 1, wherein the plurality of fourth coils includes at least five fourth coils.

7. The coiled guide lumen of claim 6, wherein the plurality of fifth coils includes at least five fifth coils.

8. The coiled guide lumen of claim 1, wherein each of the at least one first coil, the at least one second coil, the at least one third coil, the plurality of fourth coils, and the plurality of fifth coils is composed of a single length of wire.

9. The coiled guide lumen of claim 8, wherein the single length of wire has a flat cross section.

10. The coiled guide lumen of claim 8, wherein the single length of wire has a round cross section.

11. A system having a coiled guide lumen, the system comprising:
    a coiled guide lumen including:
        a longitudinal axis, the coiled guide lumen being composed of a length of wire forming a plurality of coils about the longitudinal axis;
        a first plurality of the plurality of coils having a first diameter and defining an inner lumen that is coaxial with the longitudinal axis;
        a second plurality of the plurality of coils having a second diameter that is greater than the first diameter; and
    a secondary guide lumen extending through the inner lumen;
    one or more pull wires extending through the secondary guide lumen;
    an elongate body including a proximal portion and a distal portion, the coiled guide lumen being within the elongate body and extending between the proximal portion and the distal portion; and
    a band coupled to an interior of the distal portion of the elongate body, wherein the proximal portion of the elongate body is coupled to a handle, each of the one or more pull wires including a proximal portion and a distal portion, the proximal portion of each of the one or more pull wires being in mechanical communication with the handle and the distal portion of each of the one or more pull wires being coupled to the band.

12. The system of claim 11, further comprising a shim coupled to the band, wherein the proximal portion of the elongate body is coupled to a handle, each of the one or more pull wires including a proximal portion and a distal portion, the proximal portion of each of the one or more pull wires being in mechanical communication with the handle and the distal portion of each of the one or more pull wires being coupled to the shim.

13. The system of claim 12, wherein:
    the band is a threaded annular band; and
    the shim is a flattened plate having a first edge and a second edge opposite the first edge, each of the first edge and the second edge having threading that is rotatably matable with the threaded annular band.

14. A system having a centered lumen, the system comprising:
   a coiled guide lumen defining a longitudinal axis, the coiled guide lumen being composed of a length of wire forming a plurality of coils about the longitudinal axis, the coiled guide lumen including a plurality of first sections having a first diameter and a plurality of second sections having a second diameter, the second diameter being greater than the first diameter, the plurality of first sections alternating with the plurality of second sections, and the plurality of first sections defining the centered lumen, the centered lumen being coaxial with the longitudinal axis;
   an elongate body including a proximal portion and a distal portion, the coiled guide lumen being within the elongate body and extending between the proximal portion and the distal portion;
   a secondary guide lumen extending through the centered lumen; and
   at least one pull wire extending through the secondary guide lumen and being attached at the distal portion of the elongate body.

15. A coiled guide lumen defining a longitudinal axis, the coiled guide lumen comprising:
   at least one first coil having a first outer diameter;
   at least one second coil distal to the at least one first coil and at least one third coil proximal to the at least one first coil, each of the at least one first coil and the at least one second coil having a second outer diameter, the second outer diameter being less than the first outer diameter;
   a plurality of fourth coils distal to the at least one second coil and a plurality of fifth coils proximal to the at least one third coil, each of the plurality of fourth coils and the plurality of fifth coils having a third outer diameter, the third outer diameter being less than the second outer diameter;
   a secondary guide lumen that is passed through the plurality of fourth coils and the plurality of fifth coils, such that the secondary guide lumen and the coiled guide lumen are coaxial, the secondary guide lumen being composed of a material having a low coefficient of friction including polyimide; and
   one or more pull wires extending through the secondary guide lumen.

* * * * *